United States Patent
Kelly et al.

[19]

[11] Patent Number: 6,095,809
[45] Date of Patent: Aug. 1, 2000

[54] ORTHODONTIC ARCHWIRE HAVING REDUCED STIFFNESS

[75] Inventors: John S. Kelly, Arcadia; James D. Hansen, Pasadena; James D. Cleary, Glendora, all of Calif.

[73] Assignee: 3M Innovative Properties Company, St. Paul, Minn.

[21] Appl. No.: 09/150,471

[22] Filed: Sep. 9, 1998

[51] Int. Cl.[7] .................................................. A61C 3/00
[52] U.S. Cl. .................................................................. 433/20
[58] Field of Search ................................................. 433/20

[56] References Cited

U.S. PATENT DOCUMENTS

| | | | |
|---|---|---|---|
| 2,821,020 | 1/1958 | Brusse | 32/14 |
| 3,043,007 | 7/1962 | Wallshein | 32/14 |
| 3,504,438 | 4/1970 | Wittman et al. | 32/14 |
| 4,050,156 | 9/1977 | Chasanoff et al. | 32/2 |
| 4,585,414 | 4/1986 | Kottemann | 433/20 |
| 4,659,310 | 4/1987 | Kottemann | 433/20 |
| 4,731,018 | 3/1988 | Adell | 433/20 |
| 4,850,865 | 7/1989 | Napolitano | 433/8 |
| 4,897,036 | 1/1990 | Kesling | 433/18 |
| 5,017,133 | 5/1991 | Miura | 433/20 |
| 5,137,446 | 8/1992 | Yamauchi et al. | 433/20 |
| 5,174,753 | 12/1992 | Wool | 433/8 |
| 5,203,804 | 4/1993 | Nikutowski et al. | 433/8 |
| 5,238,404 | 8/1993 | Andreiko | 433/20 |
| 5,259,760 | 11/1993 | Orikasa | 433/20 |
| 5,288,230 | 2/1994 | Nikutowski et al. | 433/20 |
| 5,454,716 | 10/1995 | Banerjee et al. | 433/20 |
| 5,456,599 | 10/1995 | Hanson | 433/8 |
| 5,468,147 | 11/1995 | Yao | 433/20 |
| 5,474,447 | 12/1995 | Chikami et al. | 433/20 |
| 5,683,245 | 11/1997 | Sacheva et al. | 433/20 |

FOREIGN PATENT DOCUMENTS

WO 97/29712  8/1997  WIPO.

*Primary Examiner*—Todd E. Manahan
*Attorney, Agent, or Firm*—James D. Christoff

[57] ABSTRACT

An orthodontic archwire with a certain cross-sectional construction has a stiffness that is less than conventional archwires having identical overall dimensions. The archwire has four corner edge portions that provide control over torquing movements and uprighting movements of the associated teeth as may be needed during the course of orthodontic treatment. The archwire is particularly useful during the early stages of orthodontic treatment when an archwire of reduced stiffness is desired and yet control over torquing and uprighting movements of the associated teeth is sought. Optionally, the archwire includes an aesthetic coating with certain characteristics that enable the majority of the coating to remain intact and provide an improved overall appearance even if certain regions of the coating are damaged and removed.

23 Claims, 3 Drawing Sheets

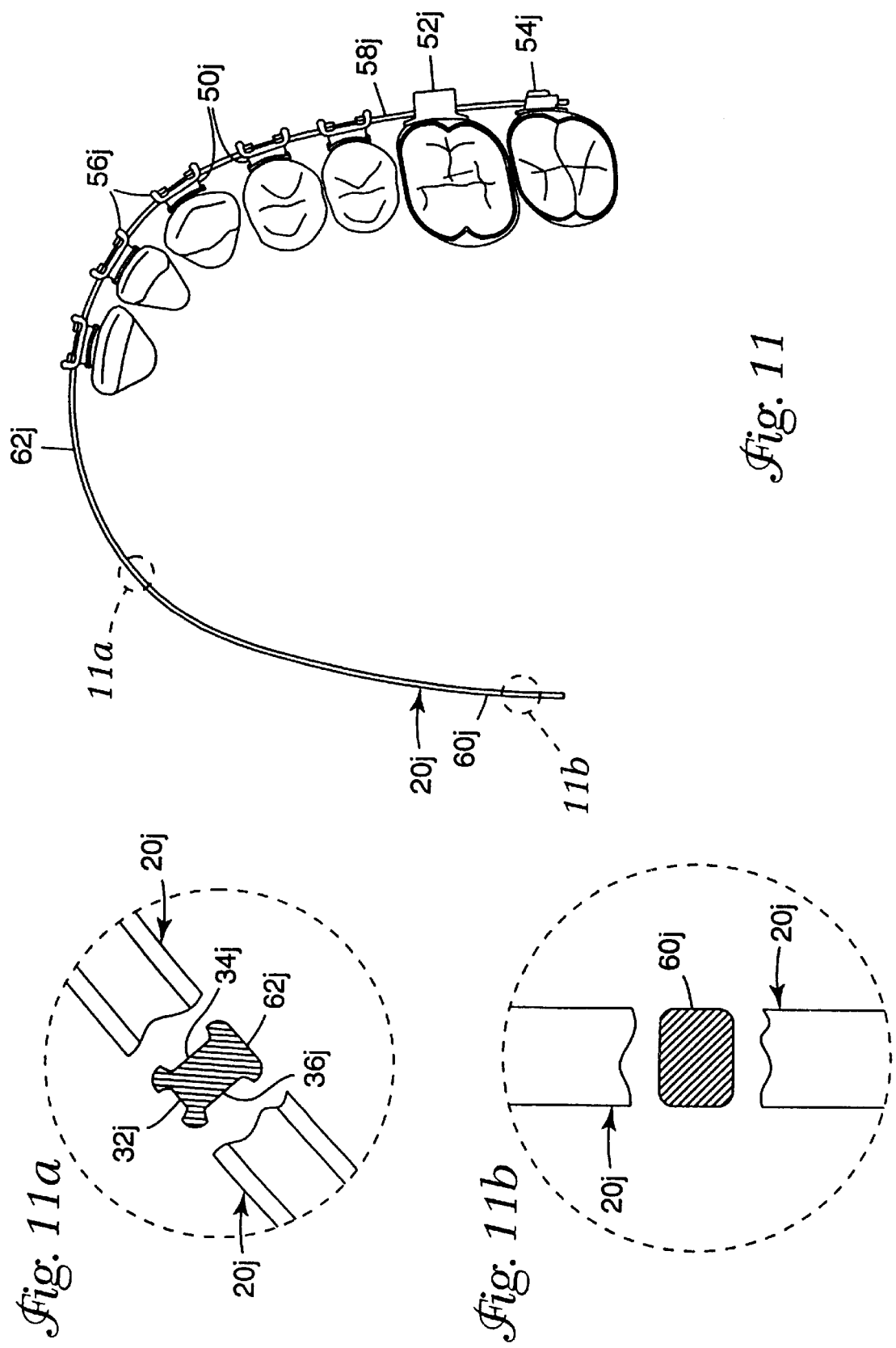

ORTHODONTIC ARCHWIRE HAVING REDUCED STIFFNESS

BACKGROUND OF THE INVENTION

1. Field of the Invention

This invention broadly relates to archwires that are used during orthodontic treatment. More particularly, this invention concerns orthodontic archwires having a reduced stiffness while also providing good control over movement of the associated teeth.

2. Description of the Related Art

Orthodontic treatment involves movement of maloccluded teeth to orthodontically correct positions. In many types of treatment, tiny slotted devices known as brackets are fixed to the patient's teeth, and a resilient archwire is inserted in the slot of each bracket. The archwire serves as a track to guide movement of the brackets so that the associated teeth are moved to desired positions.

Many commonly available orthodontic brackets have a slot with a rectangular cross-sectional configuration. The rectangular shape of the slot is adapted to mate with archwires having rectangular configurations in longitudinally transverse cross-sections. The matching, rectangular shapes of the slot and the archwire serve to non-rotatably couple each bracket to the archwire. As a consequence, the orthodontist can, if desired, twist or bend the archwire between adjacent teeth in order to impose a torquing or uprighting force on the teeth as may be needed to correct the occlusion of a particular patient.

Typically, only a single set of brackets is affixed to the patient's teeth during the course of treatment. However, the archwire may be changed at selected intervals in the treatment program and replaced with another archwire having somewhat different characteristics. For example, an archwire having a relatively low stiffness may be used initially when the teeth are located some distance from their intended final positions so that undue and possibly painful forces are not experienced by the patient. As the teeth move closer to their desired final positions, the archwire is often replaced with an archwire having a higher stiffness in order to facilitate moving the teeth over the remaining distances.

In some treatment programs, an archwire having a round cross-sectional configuration and a relatively low stiffness is used during the initial stage of treatment. Round archwires with relatively low stiffness are often used when the teeth are initially severely maloccluded, since these archwires offer little resistance to bending and can be ligated to each bracket without significant force. For example, when a pair of adjacent teeth are located labial-lingually with respect to each other (i.e., in directions along a line extending from the lips or cheeks to the tongue), low stiffness round archwires are often deemed satisfactory for moving such teeth closer together without causing undue pain to the patient. Unfortunately, round archwires can rotate in the rectangular slots of the brackets and therefore do not allow the orthodontist to apply a torquing or uprighting force as may be needed on selected teeth by placing bends or twists in the archwires.

It has been suggested in the past to modify the cross-sectional configuration of orthodontic archwires for one reason or another. For example, U.S. Pat. No. 5,468,147 describes an archwire having a substantially rectangular cross-section with longitudinal grooves extending along each of the four exterior surfaces of the archwire in order to increase the flexibility of the archwire. Orthodontic archwires with other cross-sectional configurations are described in U.S. Pat. Nos. 5,474,447, 5,456,599, 5,174,753 and 4,850,865.

In recent years, there has also been increased interest in the use of aesthetic orthodontic brackets that tend to minimize the appearance of metal in the oral cavity. For example, ceramic orthodontic brackets have now been developed that are translucent and assume the color of the underlying tooth. Translucent plastic brackets and tooth-colored plastic brackets are also known.

The use of aesthetic orthodontic brackets can present a significantly improved appearance in the oral cavity. Oftentimes, the archwire is the only metal component that is readily visible. Consequently, it would be desirable to reduce or eliminate this last remaining metallic appearance at least from anterior teeth if possible.

Orthodontic archwires that are coated with a non-metallic aesthetic layer have been proposed in the past. For example, U.S. Pat. No. 5,454,716 and PCT published application No. WO 97/29712 describe orthodontic archwires that are coated with a thin coloring layer that matches the color of the teeth. Other coated orthodontic archwires are described in U.S. Pat. Nos. 4,050,156 and 3,504,438. U.S. Pat. No. 4,731,018 describes an archwire with a metal part and a plastic part arranged so that the plastic part faces in a labial direction.

SUMMARY OF THE INVENTION

The present invention is directed to an orthodontic archwire that provides the mechanical benefits of rectangular archwires and yet also has a certain construction that reduces stiffness of the archwire along all or at least a portion of its length. The archwire of the present invention can be used during early stages of treatment because of its reduced stiffness, and yet provides good control over torquing or uprighting movements of the associated teeth in a manner similar to the control provided by conventional, rectangular archwires.

In one aspect of the invention, the orthodontic archwire has a central, elongated axis along with a labial-occlusal corner edge portion, a labial-gingival corner edge portion, a lingual-occlusal corner edge portion and a lingual-gingival corner edge portion. The archwire has an elongated labial recess located lingually of the labial-occlusal corner edge portion and the labial-gingival corner edge portion. The archwire has a generally flat lingual side that extends from the lingual-occlusal corner edge portion to the lingual-gingival corner edge portion.

Another aspect of the present invention relates to an orthodontic archwire that includes a substrate having a central elongated axis. The substrate has a labial-occlusal corner edge portion, a labial-gingival corner edge portion, a lingual-occlusal corner edge portion and a lingual-gingival corner edge portion. The substrate has an elongated labial recess located lingually of the labial-occlusal corner edge portion and the labial-gingival corner edge portion. The archwire also includes a coating that is fixed to the substrate and is located in the labial recess.

Another aspect of the present invention concerns an orthodontic archwire that comprises a substrate and a coating connected to the substrate. The coating is connected to the substrate with a certain adhesive strength, and the coating has a cohesive strength that is less than the adhesive strength.

The present invention is also directed to an orthodontic archwire having a lingual portion and a labial portion spaced from the lingual portion. Each of the lingual portion and the labial portion having a certain modulus of elasticity. The archwire also includes an intermediate portion interconnecting the labial portion and the lingual portion. The intermediate portion has a modulus of elasticity that is lower than the modulus of elasticity of the lingual portion and the modulus of elasticity of the labial portion.

These and other aspects of the invention are described in the various embodiments set out in detail below and are shown in the accompanying drawings.

BRIEF DESCRIPTION OF THE DRAWINGS

FIG. 11 is an enlarged view looking in a gingival direction toward another orthodontic archwire of the invention, wherein the archwire is connected to exemplary orthodontic brackets affixed to respective teeth for purposes of illustration, and wherein a substrate of the archwire has a different configuration in distal end sections of the archwire than its configuration in an anterior section of the archwire; and FIGS. 11a and 11b are enlarged views taken at the locations designated 11a and 11b respectively in FIG. 11, showing views looking in a gingival direction as well as cross-sectional views of the archwire at those locations.

DETAILED DESCRIPTION OF THE PREFERRED EMBODIMENTS

Figure 1:
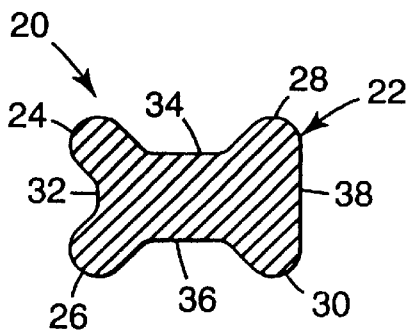
FIG. 1 is an enlarged cross-sectional view of an orthodontic archwire constructed in accordance with one embodiment of the invention, wherein the archwire has recesses extending along its occlusal, labial and gingival sides.

An orthodontic archwire according to one embodiment of the invention is illustrated in FIG. 1 and is designated broadly by the numeral 20. The archwire 20 includes a substrate 22 that is elongated in a direction perpendicular to the plane of the cross-sectional view shown in FIG. 1.

The substrate 22 has a labial-occlusal corner edge portion 24 and a labial-gingival corner edge portion 26. The substrate 22 also includes a lingual-occlusal corner edge portion 28 and a lingual-gingival corner edge portion 30. As illustrated in FIG. 1, the four corner portions, 24, 26, 28, 30 are arranged in a rectangular array when viewed in direction normal to the logitudinal axis of the archwire 20. Preferably, each of the corner edge portions 24, 26, 28, 30 has a curved periphery as shown in FIG. 1 with a radius of curvature that is similar or identical to the radius of the rounded corners of conventional rectangular archwires. An example of a suitable radius is 0.003 inch (0.076 mm); an example of suitable overall dimensions of the archwire 20 is 0.025 inch (0.635 mm) by 0.0175 inch (0.44 mm).

The substrate 22 has a labial recess 32 that extends on the labial side of the substrate 22 between the labial-occlusal corner edge portion 24 and the labial-gingival corner edge portion 26. As can be appreciated by reference to FIG. 1, the bottom or lingual side of the labial recess 32 is located lingually of a hypothetical reference plane that extends between the labial-most regions of the labial-occlusal corner edge portion 24 and the labial-gingival corner edge portion 26.

The substrate 22 also has an occlusal recess 34 that is located on an occlusal side of the substrate 22 between the labial-occlusal corner edge portion 24 and the lingual-occlusal corner edge portion 28. The bottom or gingival side of the recess 34 is located gingivally of a hypothetical reference plane that extends between the occlusal-most regions of the labial-occlusal corner edge portion 24 and the lingual-occlusal corner edge portion 28.

A gingival recess 36 extends along the gingival side of the substrate 22 in a location between the labial-gingival corner edge portion 26 and the lingual-gingival corner edge portion 30. The bottom or occlusal side of the gingival recess 36 is located occlusally of a hypothetical reference plane that extends between the gingival-most regions of the labial-gingival corner edge portion 26 and the lingual-gingival corner edge portion 30.

The recesses 32, 34, 36 are elongated and extend in directions parallel to the central longitudinal axis of the substrate 22 as well as to the longitudinal axes of the corner edge portions 24, 26, 28, 30. Optionally, but not necessarily, the recesses 34, 36 have a cross-sectional area that is identical and somewhat larger than the cross-sectional area of the recess 32.

A lingual side 38 of the substrate 22 is flat and lacks a recess. The lingual side 38 lies in a hypothetical reference plane that extends between the lingual-most regions of the lingual-occlusal corner edge portion 28 and the lingual-gingival corner edge portion 30.

The recesses 32, 34, 36 reduce the overall stiffness of the archwire 20 and increase the malleability of the archwire 20. The recesses 32, 34, 36 allow the archwire 20 to be readily deformed by compressive stresses as may be induced, for example, during bending of the archwire 20 by a hand instrument. The recesses 32, 34, 36 increase the likelihood that a hand instrument used for bending the archwire 20 will contact the archwire 20 only at the corner edge portions 24, 26, 28, 30, causing relatively high contact stresses to occur in the corner edge portions 24, 26, 28, 30 as the archwire 20 is bent. The recesses 32, 34, 36 promote localized buckling of adjacent corner edge portions when the archwire 20 is bent with the result that permanent bends are easily formed as may be desired. The remainder of the archwire 20 which has not been subjected to localized buckling continues to exhibit a relatively low stiffness due to a reduction in the moment of inertia that is caused by the provision of the recesses 32, 34, 36. The remainder of the archwire 20 which has not been subjected to localized bending also exhibits a relatively long working range.

The four corner edge portions 24, 26, 28, 30 also provide good control over torquing and uprighting movements of the associated tooth in a manner similar to the control provided by conventional archwires having a solid, rectangular cross-section. For example, a bend or twist in the archwire can cause one or more of the corner edge portions 24, 26, 28, 30 to exert a force on adjacent regions of the bracket slot which, in turn, urges a somewhat similar force on the associated tooth.

The recesses 32, 34, 36 enable the archwire 20 to have a smaller moment of inertia and thus a reduced stiffness in comparison to a conventional rectangular archwire of similar overall dimensions with a solid cross-section. As a result, the archwire 20 may have relatively large overall dimensions that essentially fill the slots of the brackets and yet have a relatively low stiffness that is suitable for use in earlier treatment stages in comparison to a conventional rectangular archwire having a solid cross-sectional construction. The archwire 20 of the present invention also enables the orthodontist to have control over torquing and uprighting movements of the associated teeth at an earlier stage in the treatment program.

The flat lingual side 38 is an advantage because it flatly contacts the lingual wall of the archwire slots of the brackets. Such flat contact provides good engagement of the archwire 20 with the brackets and enhances control over movement of the teeth. Additionally, elimination of a recess on the lingual side 38 eases manufacture of the archwire 20.

Suitable materials for the substrate 22 include stainless steel such as AISI 300 series including type 304V, precipitation-hardening type stainless steels such as 17-7pH, cobalt chromium alloys such as Elgiloy brand alloy, shape-memory alloys such as nickel-titanium and ternary-substitution nickel-titanium alloys, and titanium alloys such as beta-titaniums.

The recesses 32, 34, 36 may be made by various techniques, including processes such as drawing a wire through certain form dies, rolling a wire through contoured rolls, laser machining or photoetching. The use of laser machining and photoetching techniques have an additional advantage, in that the cross-sectional configuration of the archwire 20 can be easily selectively modified in different portions along the length of the archwire as will be described below in connection with FIG. 11.

The photoetching technique of making the recesses 32, 34, 36 includes the step of covering all four sides of a wire in a photo-curable material that is resistant to acid once cured. Regions of the wire that are to be removed are masked while remaining regions of the wire are exposed to light. Next, the unexposed, uncured regions of the mask are dissolved away. A concentrated acid is then used to etch the wire in areas where the mask was removed. Finally, the remaining portions of the mask are stripped away with a suitable solvent to yield the desired finished geometry.

Figure 2:
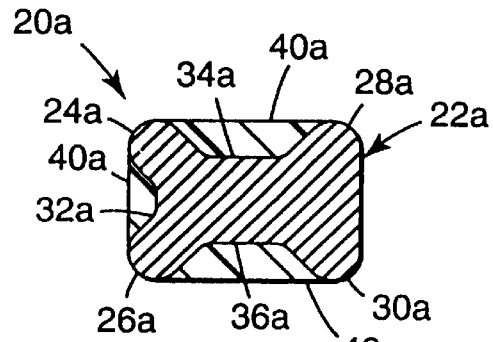
FIG. 2 is a view of an orthodontic archwire in accordance with another embodiment of the invention, wherein an aesthetic coating is located in recesses of a substrate of the archwire.

Another embodiment of the invention is shown in FIG. 2, wherein an archwire 20a includes a substrate 22a as well as a coating 40a. The substrate 22a is identical to the substrate 22 described earlier, and as such a detailed description of the substrate 22a will not be provided.

The coating 40a is fixed to the substrate 22a and is located in recesses 32a, 34a, 36a. In the embodiment shown, the coating 40a fills the recesses 32a, 34a, 36a and presents an exterior surface that is flush with outer regions of adjacent corner portions 24a, 26a, 28a, 30a. As an alternative, the coating 40a only partially fills the recesses 32a, 34a, 36a and presents an exterior surface having a slight concavity. A slight concavity in the exterior surface of the coating 40a reduces contact of the coating 40a with the brackets, and therefore reduces the possibility that substantial areas of the coating 40a are abraded away as the brackets move along the archwire 20a.

Preferably, the coating 40a presents an appearance that matches the color of the underlying teeth so that the visibility of the archwire 20a in the oral cavity is substantially reduced in comparison to, for example, a metallic archwire of similar overall dimensions. Examples of suitable colors include off-white shades and the various tooth-colored shades of the Vita scale. Alternatively, coatings presenting bright, highly apparent colors may be preferred (such as red, blue, green or neon shades) particularly by younger patients, and optionally chosen to match or contrast with colors selected for elastic ligatures.

Suitable compositions for the coating 40a include paints, inks and the like. For example, the coating 40a may be made of a resin binder and an opacifying filler. Suitable resins include acrylics, methacrylics, epoxies, liquid crystal polymers, acetals, nylons, polyurethanes, polysulfones, polyamides, polyimids, polyacetates, phenolics, polyesters and amino type resins such as melamine formaldehyde and urea formaldehyde, and combinations thereof.

Suitable fillers for the coating 40a include aluminum oxide, zirconium oxide, titanium dioxide, silicone dioxide and boron nitride. The size of the filler particles should be very small since the coating 40a may be quite thin in certain areas. An example of a suitable filler particle size is less than 5 micron, and preferably less than 1 micron.

Other suitable compositions for the coating 40a are described in U.S. Pat. No. 5,454,716 and in PCT published application No. WO 97/29712, both of which are incorporated by reference. The coating 40a may also include a fluoride releasing compound such as sodium fluoride, potassium fluoride, zinc fluoride or fluoralumino silicates.

Preferably the coating 40a is highly resistant to staining by food and beverages so that the coating 40a does not significantly discolor while the archwire 20a resides in the oral cavity. For example, the coating 40a should be resistant to staining by mustard, ketchup, cranberry juice, tea, curry powders, blueberries, coffee and the like. Suitable coatings do not show any significant staining after immersion of the archwire 20a in such materials for 24 hours.

The coating 40a may be applied to the substrate 22a by various techniques including spraying, wiping, electrostatic coating, electrolytic coating, electrophoresis coating, vacuum surface coating and/or any of the various processes described in the aforementioned U.S. Pat. No. 5,454,716 and PCT published application No. WO 97/29712. The coating 40a may be applied as a single layer or in a plurality of layers, and is optionally fully or partially cured between applications of successive layers. Preferably, at least the topcoat layer is significantly resistant to staining by food and beverages as described above.

As other options, the coating 40a may be a hard carbon coating or may comprise one or more of the coating compositions described earlier in combination with a topcoat made of a hard carbon coating. Suitable hard carbon coatings and application techniques are described, for example, in U.S. Pat. Nos. 5,203,804 and 5,288,230, both of which are incorporated by reference herein.

The recesses 32a, 34a, 36a provide an advantage in that the coating 40a is substantially protected from contact stresses that may be present between the archwire 20a and engaged regions of the orthodontic brackets. As a general rule, the highest contact stresses exerted on the archwire 20a during the course of orthodontic treatment are exerted on regions of one or more of the four corner edge portions 24a, 26a, 28a, 30a rather than on regions of the coating 40a. As a result, the substrate 22a rather than the coating 40a bears the brunt of such contact stresses and reduces damage that might otherwise be inflicted on the coating 40a. A concavity in the outer surface of the coating 40a as described above also helps to avoid contact between the coating 40a and the brackets.

The substrate 22a may be made of a metallic material such as stainless steel, nickel-titanium, beta-titanium or other alloys as described above. If the metallic material has a hardness and/or compressive strength greater than the hardness and/or compression strength respectively of the coating 40a, the corner edge portions 24a, 26a, 28a, 30a function as strong load-bearing regions where torquing or uprighting forces can be passed to the brackets. Moreover, since at least some of the corner edge portions 24a, 26a, 28a, 30a are in contact with the bracket, the archwire 20a exhibits sliding friction characteristics that are similar to the sliding friction characteristics of a conventional metallic archwire having a solid, rectangular cross-sectional configuration.

Preferably, the adhesive strength of the coating 40a to the substrate 22a is greater than the cohesive strength of the coating 40a. Consequently, the concave walls of the substrate 22a defining the recesses 32a, 34a, 36a tend to remain covered by at least a portion of the coating 40a even if outer sections of the coating 40a are damaged and chipped away. For example, if the archwire 20a is bent to such an extent that localized buckling of the substrate 22a occurs and adjacent regions of the coating 40a fracture, the coating 40a will tend to break away in small chips from itself rather than separate from the substrate 22a. Since the substrate 22a remains covered in such instances by the coating 40a, the aesthetic qualities of the archwire 20a are not unduly diminished.

To determine whether the adhesive strength of the coating 40a to a substrate is greater than the cohesive strength of the coating 40a, a quantity of the coating material is used to bond two test pieces of substrate material together. Once the coating material has cured, the test pieces are pulled apart from each other and inspected. If the coating has fractured within itself in a manner such that a portion of the coating remains on both of the test pieces, one can conclude that the cohesive strength of the coating is less than the adhesive strength of the coating to the test pieces.

Optionally, a coupling agent may be used to enhance adhesion of the coating 40a to the substrate 22a. When the substrate 22a is a metallic material, suitable coupling agents include zirconates, aluminates and titanates or combinations thereof.

Alternatively, an organofunctional silane may be utilized as a coupling agent to enhance adhesion of the coating 40a to the substrate 22a. Suitable siline coupling agents and other coupling agents are described in the aforementioned U.S. Pat. No. 5,454,716.

The coupling agents provide significant benefits in addition to the benefit of improved adhesion of the coating 40a to the substrate 22a. In particular, the use of a coupling agent can lower the viscosity of the coating material during application and while still liquid, so that the coating material can be applied to the substrate 22a in a relatively thin layer of precise thickness. Coupling agents can also serve to lower the curing temperature of the polymeric coating materials so that the substrate 22a need not be exposed to relatively high temperatures during curing of the coating material. As a result, the mechanical characteristics of the substrate 22a are not significantly impaired during exposure to heat as may be needed to cure the coating material.

Roughening the surface of the substrate 22a can also enhance the adhesion of the coating 40a to the substrate 22a. Suitable techniques for roughening the substrate 22a include grit blasting and chemical etching.

Figure 3:
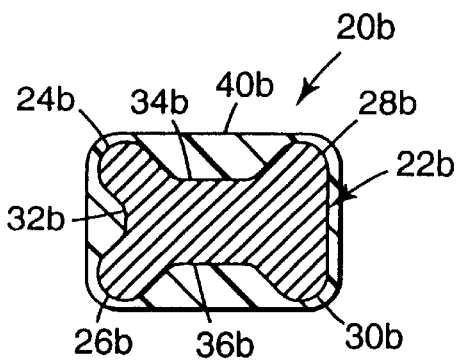
FIG. 3 is an enlarged, cross-sectional view of an orthodontic archwire constructed in accordance with another embodiment of the invention, wherein the archwire includes an aesthetic coating that is located in recesses of a substrate and the coating also extends over the entire remaining periphery of the substrate.

An orthodontic archwire 20b according to another embodiment of the invention is shown in FIG. 3 and includes a substrate 22b that is identical to the substrates 22, 22a described earlier. The substrate 22b has four corner edge portions 24b, 26b, 28b, 30b that are identical to the corner edge portions 24, 26, 28, 30 respectively. Additionally, the substrate 22b includes recesses 32b, 34b, 36b that are identical to the recesses 32, 34, 36 respectively.

A coating 40b is received in the recesses 34b, 36b, 38b in a manner similar to the coating 40a of the archwire 20a. However, the coating 40b also covers, at least initially, the four corner edge portions 24b, 26b, 28b, 30b. Preferably, the coating 40b is relatively thin in regions adjacent the corner edge portions 24b, 26b, 28b, 30b. In this manner, the overall size of the substrate 22b need not be significantly reduced so that the modulus of elasticity of the archwire 20b remains within a satisfactory range.

The thickness of the coating 40b shown in FIG. 3 adjacent the corner edge portions 24b, 26b, 28b, 30b should not be considered as drawn to scale, since it may be thinner or thicker than illustrated. For example, the thickness of the coating 40b in areas extending over the four corner edge portions 24b, 26b, 28b, 30b is preferably less than 12 microns. As an option, the majority of the coating that is located within the recesses 34b, 36b, 38b may have a different composition than the composition of the coating extending over the corner edge portions 24b, 26b, 28, 30b. For example, the coating 40b may be made by applying a mixture of a resin binder and an opacifying filler of the types mentioned above to the recesses 34b, 36b, 38b, curing the resin binder and filler mixture, and then applying a hard carbon coating over the entire periphery of the archwire 20b including areas over the cured resin binder and filler mixture as well as over the corner edge portions 24b, 26b, 28b, 30b.

During use of the archwire 20b, portions of the coating 40b that extend over the edge portions 24b, 26b, 28b, 30b may be subject to high contact stresses as a result of sliding contact of the archwire 20b with orthodontic brackets or other appliances. Those portions of the coating 40b may fracture and break away from remaining portions of the coating 40b. However, since the adhesive strength of the coating 40b to the substrate 22b is preferably greater than the cohesive strength of the coating 40b, such areas that are subject to relatively high contact stresses tend to break away, if at all, in relatively small pieces or chips and leave the remainder of the coating 40b substantially intact and undamaged. As a consequence, the majority of the archwire 20b remains covered by the coating 40b so that the aesthetic characteristics of the archwire 20b are not significantly impaired.

Figure 4:
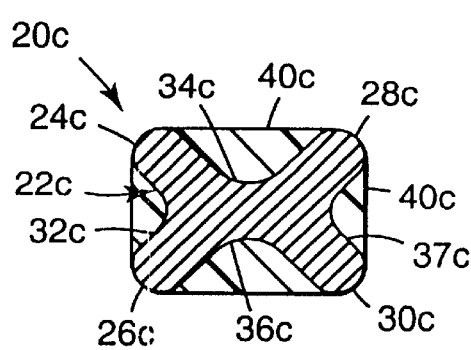
FIG. 4 is an enlarged, cross-sectional view of an archwire constructed in accordance with another embodiment of the invention, wherein a substrate of the archwire has four recesses and a coating is located in each of the recesses.

The orthodontic archwire 20c that is depicted in FIG. 4 represents another embodiment of the present invention. The archwire 20c includes a substrate 22c with four corner edge portions 24c, 26c, 28c, 30c. The archwire 20c also has a labial recess 32c, an occlusal recess 34c and a gingival recess 36c. In addition, a lingual side of the archwire 20c has a lingual recess 37c with a bottom or labial-most most surface that is located labially of outermost regions of the edge portions 28c, 30c.

The archwire 20c also has a coating 40c that is fixed to the substrate 22c and is located in each of the recesses 32c, 34c, 36c, 37c. Optionally, the coating 40c may also extend in a thin layer over the four corner edge portions 24c, 26c, 28c, 30c. The substrate 22c and the coating 40c are preferably similar in composition and in method of manufacture to the compositions and manufacturing methods described above in connection with the substrates 22, 22a and the coating 40a.

Figure 5:
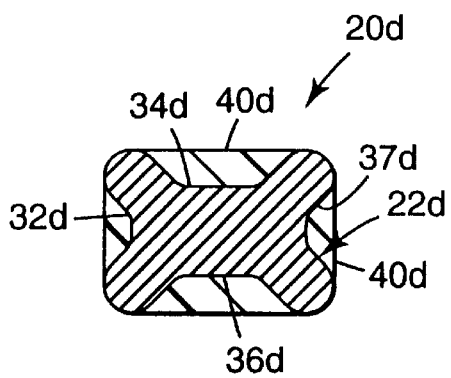
FIG. 5 is an enlarged, cross-sectional view of an archwire according to another embodiment of the invention, wherein a substrate of the archwire has four recesses with a somewhat different configuration than the recesses of the substrate depicted in FIG. 4.

Another embodiment of the invention is depicted in FIG. 5, wherein an archwire 20d includes a substrate 22d and a coating 40d. The substrate 22d is somewhat similar to the substrate 22c, in that the substrate 22d includes four recesses 32d, 34d, 36d, 37d. However, the cross-sectional configuration of the substrate 22d is somewhat different than the cross-sectional configuration of the substrate 22c as can be observed by comparison of FIG. 5 to FIG. 4.

The coating 40d is received in each of the recesses 32d, 34d, 36d, 37d and optionally extends over the four corner edge portions of the substrate 22d in a thin layer. Preferably the composition and method of manufacture of the substrate 22d and coating 40d are similar to the compositions and method of manufacture described above in connection with the substrates 22, 22a and the coating 40a.

Figure 6:
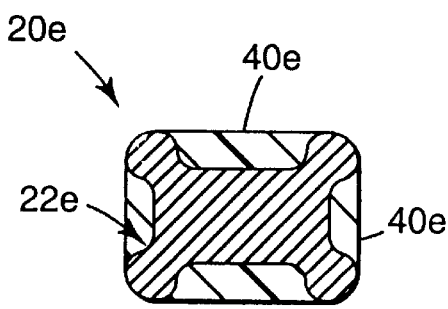
FIG. 6 is an enlarged, cross-sectional view of an orthodontic archwire according to still another embodiment of the invention, wherein a substrate of the archwire has recesses with another configuration.

An orthodontic archwire 20e as illustrated in FIG. 6 is constructed according to another embodiment of the invention and includes a substrate 22e and a coating 40e. The archwire 20e is essentially the same as the archwire 20d, except that the total area of the recesses of the substrate 22e is larger than the total area of the recesses of the substrate 22d when considered in longitudinally transverse cross-sections (i.e. in cross-sections parallel to the plane of the drawing of FIG. 6). As a consequence, the amount of space occupied by the substrate 22e is reduced and the stiffness of the archwire 20e will change correspondingly. For example, if the substrates 22d, 22e are both made of the same metallic material and if the coatings 40d, 40e are both made of a different material that has a lower modulus of elasticity than the modulus of elasticity of the metallic material, the archwire 22e will have less stiffness than the archwire 20d.

Figure 7:
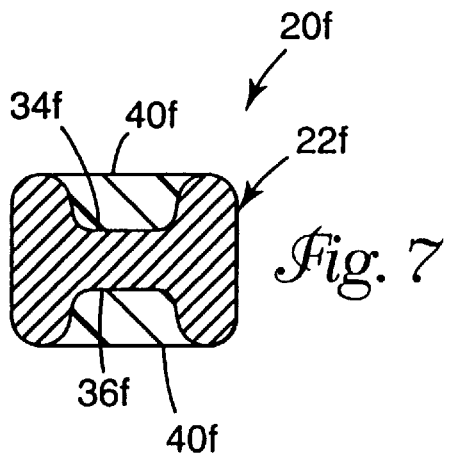
FIG. 7 is an enlarged, cross-sectional view of an orthodontic archwire according to yet another embodiment of the invention, wherein a substrate of the archwire is provided with an occlusal and a gingival recess.

FIG. 7 represents another embodiment of the invention, wherein an orthodontic archwire 20f includes a substrate 22f with an occlusal recess 34f and a gingival recess 36f. In this embodiment, the cross-sectional configuration of the substrate 22f is somewhat "H"-shaped and lacks a labial recess and a lingual recess. A lingual side of the substrate 22f extends in a flat plane between lingual-most regions of the lingual corner edge portions, so that the archwire 20f flatly contacts the bottom or lingual side of the archwire slots of the brackets.

Optionally, the archwire 20f includes a coating 40f that is received in the occlusal recess 34f and the gingival recess 36f. Although not shown, as another option the coating 40f also extends around the entire periphery of the substrate 22f including the labial and lingual sides.

The archwire 20f illustrated in FIG. 7 is an advantage because it is relatively easy to manufacture. Additionally, the flat lingual side of the substrate 22f provides a good bearing surface for contact with the associated brackets.

Figure 8:
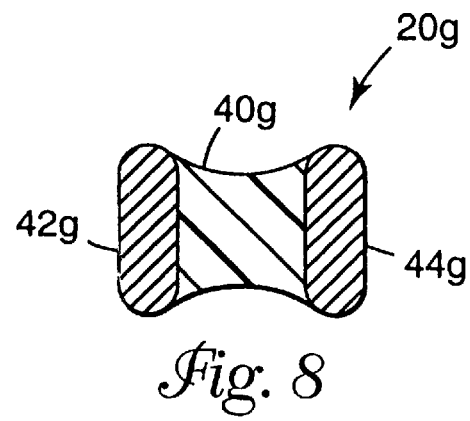
FIG. 8 is an enlarged, cross-sectional view of an orthodontic archwire in accordance with an additional embodiment of the invention, wherein a high modulus labial working portion and a high modulus lingual working portion are fixed to each other by an intermediate low modulus binder.

An orthodontic archwire 20g constructed in accordance with yet another embodiment of the invention is depicted in FIG. 8 and includes a labial substrate portion 42g and a lingual substrate portion 44g that is spaced from the labial substrate portion 42g. The archwire 20g also includes an intermediate portion or coating 40g that extends across substantially the entire inner, facing surfaces of the portions 42g, 44g and also serves to affix the portions 42g, 44g together.

Preferably, the modulus of elasticity of the intermediate portion or coating 40g is less than the modulus of elasticity of either of the portions 42g, 44g. Such construction is an advantage in instances where an archwire with a relative low modulus of elasticity is desired. Yet, the portions 42g, 44g can be made, for example, of a metallic material to provide good bearing surfaces for contact with the brackets.

Preferably, the intermediate portion or coating 40g is similar in composition and method of manufacture to the coating 40a described above. The portions 42g, 44g may have a composition similar to the composition of the substrate 22 described above. Optionally, the coating 40g may extend around the entire periphery of the archwire 20g, including in a thin layer across the labial and lingual sides of the portions 42g, 44g respectively. Optionally, the entire periphery of the archwire 20g can be covered with a hard carbon coating as described above.

Figure 9:
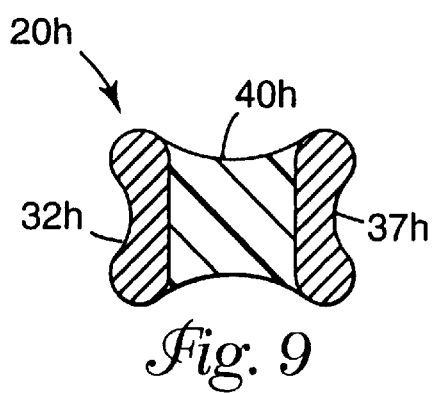
FIG. 9 is an enlarged, cross-sectional view of an orthodontic archwire in accordance with yet another embodiment of the invention that is somewhat similar to the embodiment illustrated in FIG. 8 but also includes longitudinal outer recesses extending along the lingual working portion and the labial working portion.

An orthodontic archwire 20h constructed in accordance with another embodiment of the invention is shown in FIG. 9. The archwire 20h is essentially the same as the archwire 20g depicted in FIG. 8, except that the archwire 20h has a labial recess 32h and a lingual recess 37h in the labial and lingual portions respectively. Optionally, one or both of the recesses 32h, 37h can be filled with a coating such as the coating 40g.

Figure 10:
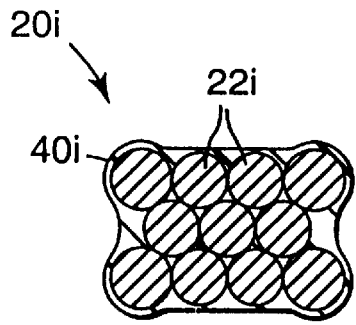
FIG. 10 is an enlarged, cross-sectional view of an orthodontic archwire according to an additional embodiment of the invention, wherein a plurality of high modulus working portions are arranged in a generally rectangular array and are surrounded by a low modulus binder portion.

FIG. 10 represents another embodiment of the invention, wherein an orthodontic archwire 20i includes a number of internal substrates 22i that are preferably closely packed together in a generally rectangular array. The substrates 22i can each have a circular cross-sectional configuration as depicted, or have another type of cross-sectional configuration such as square, rectangular, hexagonal or the like. The substrates 22i may have identical cross-sectional areas or have somewhat different cross-sectional areas in accordance with their location within the archwire 20i. The substrates 22i extend in parallel paths, although as another option the substrates 22i are wound about each other along their lengths in a twisted or braided fashion.

The substrates 22i are covered with a coating 40i that preferably extends around the entire periphery of the archwire 20i. Optionally, and as shown, a labial side and a lingual side of the archwire 20i each include a curved recess. The coating 40i has a modulus of elasticity that is less than the modulus of elasticity of the substrates 22i. The composition of the substrates 22i and the coating 40i are preferably similar to the composition of the substrates 20g and the coating 40g described above.

Preferably, although not necessarily, the four substrates 22i that are located along the four corners of the archwire 20i have an overall dimension or diameter that is slightly larger than the over dimension or diameter of the remaining substrates 22*i* as illustrated in FIG. 10. As a consequence, the four corner substrates 22*i* protrude past the remaining substrates 22*i* and thus bear the majority of the contact forces with the archwire slots of associated brackets in most instances. Additionally, such construction reduces contact of the bracket with the coating 40*i* in areas between the four corner substrates 22*i*, such that the possibility of undue wear or abrasion of the coating 40*i* in those areas is also diminished correspondingly.

The configurations and constructions of the various embodiments as described above can extend along the entire length of the archwire, or optionally may be present in only certain sections of the archwire. An example of the latter feature is shown in FIG. 11, wherein an archwire of the invention has been designated by the numeral 20*j*. However, it should be understood in this regard that any of the archwires described above including the archwires 20–20*i* may be substituted for the archwire 20*j* in FIG. 11.

The archwire 20*j* is received in slots of orthodontic brackets 50*j* as well as in passages of buccal tube appliances 52*j*, 54*j*. The archwire 20*j* is releasably connected to the brackets 50*j* by elastic O-ring ligatures 56*j*. Each of the brackets 50*j* and the buccal tube appliances 52*j*, 54*j* are affixed to respective teeth of the patient. (For purposes of illustration, only half of the patient's teeth, brackets and buccal tube appliances are shown in FIG. 11.)

The archwire 20*j* has an overall, generally U-shaped configuration when viewed looking in a gingival direction from an occlusal plane, as is illustrated in FIG. 11. The U-shaped archwire 20*j* has a pair of spaced apart distal end sections 58*j*, 60*j* that are interconnected by an anterior section 62*j*.

The anterior section 62*j* has a substrate with a labial recess 32*j*, an occlusal recess 34*j* and a gingival recess 36*j* as shown in the upper enlarged portion of FIG. 11. By contrast, both of the distal end sections 58*j*, 60*j* have a substrate with a solid cross-sectional configuration as shown in the lower enlarged portion of FIG. 11. As a result, the anterior section 62*j* has a stiffness that is less than the stiffness of either of the distal end sections 58*j*, 60*j*. Expressed another way, the anterior section 62*j* has a greater working range than the working range of either of the distal end sections 58*j*, 60*j*.

The location of the transition from the anterior section 62*j* to either of the distal end sections 58*j*, 60*j* can be selected as needed for a particular patient. For example, and as shown in FIG. 11, the transition from the anterior section 62*j* to the distal end sections 58*j*, 60*j* can occur at a location between the patient's cuspid teeth and the adjacent bicuspid teeth. Other transition locations are also possible. The transitions could occur abruptly, in stages or phased in gradually along the length of the archwire 20*j*. Moreover, the length of certain recesses could be longer than the length of other recesses. For example, the labial recess 32*j* may extend distally beyond the occlusal recess 34*j* and the distal recess 36*j* so that only the labial recess 32*j* is present in the transition regions.

Although not shown in the drawings, the archwire 20*j* may include a coating similar to the coatings described above along all or only a portion of its length.

As other alternatives, the archwire 20*j* may include a length or lengths of rectangular hollow tubing that extends over all or part of the substrate. For example, the hollow tubing could cover the distal end sections 58*j*, 60*j* to increase the stiffness of those sections, while the anterior section 62*j* could be devoid of tubing. Such construction could simplify manufacture, since the cross-sectional configuration of the substrate could optionally be uniform along its entire length.

Those skilled in the art may recognize that a number of additions and modifications may be made to any of the various embodiments described above without departing from the essence of the invention. Accordingly, the invention should not be deemed limited to the presently preferred embodiments that are described above in detail, but instead only by a fair scope of the claims that follow along with their equivalents.

We claim:

1. An orthodontic archwire having a central, elongated axis and an overall generally "U"-shaped configuration with a concave lingual side, the archwire having a labial-occlusal corner edge portion, a labial-gingival corner edge portion, a lingual-occlusal corner edge portion and a lingual-gingival corner edge portion, the archwire having an elongated labial recess located lingually of the labial-occlusal corner edge portion and the labial-gingival corner edge portion, wherein the corner edge portions are arranged in a rectangular array when viewed in directions normal to the axis and wherein the lingual side is generally flat and extends from the lingual-occlusal corner edge portion to the lingual-gingival corner edge portion.

2. The orthodontic archwire of claim 1, and including a coating located in the labial recess.

3. The orthodontic archwire of claim 2, wherein the coating presents a generally tooth-colored appearance.

4. The orthodontic archwire of claim 2, wherein the archwire has an overall, generally U-shaped configuration with a pair of distal end sections and an anterior section interconnecting the distal end sections, and wherein the distal end sections have a stiffness greater than the stiffness of the anterior section.

5. The orthodontic archwire of claim 2, wherein the archwire also has an elongated occlusal recess located gingivally of the labial-occlusal corner edge portion and the lingual-occlusal corner edge portion and a gingival recess that is located occlusally of the labial-gingival corner edge portion and the lingual-gingival corner edge portion.

6. An orthodontic archwire comprising:

a substrate having a central, elongated axis and an overall, generally "U"-shaped configuration with a concave lingual side, the substrate having a labial-occlusal corner edge portion, a labial-gingival corner edge portion, a lingual-occlusal corner edge portion and a lingual-gingival corner edge portion, the substrate having an elongated labial recess located lingually of the labial-occlusal corner edge portion and the labial-gingival corner edge portion and wherein corner edge portions are arranged in a rectangular array when viewed in directions normal to the axis; and a coating fixed to the substrate and located in the labial recess.

7. The orthodontic archwire of claim 6, wherein the coating has a certain modulus of elasticity, and wherein the substrate has a modulus of elasticity that is greater than the modulus of elasticity of the coating.

8. The orthodontic archwire of claim 6, wherein the coating presents a generally tooth-colored appearance.

9. The orthodontic archwire of claim 6, wherein the substrate also has a elongated occlusal recess located gingivally of the labial-occlusal corner edge portion and the lingual-occlusal corner edge portion, and a gingival recess that is located occlusally of the labial-gingival corner edge portion and the lingual-gingival corner edge portion, and wherein the coating is also located in the occlusal recess and the gingival recess.

10. The orthodontic archwire of claim 6, wherein the coating is connected to the substrate with a certain adhesive strength, and wherein the coating has a certain cohesive strength that is less than the adhesive strength.

11. The orthodontic archwire of claim 6, including a coupling agent comprising a titanite to enhance adhesion of the coating to the substrate.

12. The orthodontic archwire of claim 6, whrein the archwire has an overall-generally U-shaped configuration with a pair of distal end sections and an anterior section interconnecting the distal end sections, and wherein the recess extends only in the anterior section.

13. The orthodontic archwire of claim 6, wherein the substrate has a lingual side that extends in a reference plane from lingual-most regions of the lingual-occlusal corner edge portion and of the lingual-gingival corner edge portion.

14. An orthodontic archwire comprising:

a substrate; and a coating connected to the substrate, wherein the coating is connected to the substrate with a certain adhesive strength, and wherein the coating has a cohesive strength that is less than the adhesive strength.

15. The orthodontic archwire of claim 14, wherein the coating comprises a polymer.

16. The orthodontic archwire of claim 14, and including a titanite coupling agent to enhance adhesion of the coating to the substrate.

17. The orthodontic archwire of claim 14, wherein the substrate includes at least one elongated recess, and wherein the coating is located in at least one recess.

18. An orthodontic archwire having a lingual portion and a labial portion spaced from the lingual portion, each of the lingual portion and the labial portion having a certain modulus of elasticity, the archwire also including an intermediate portion interconnecting the labial portion and the lingual portion and having a composition different than the composition of the labial portion and the lingual portion, the intermediate portion having a modulus of elasticity that is lower than the modulus of elasticity of the lingual portion and the modulus of elasticity of the labial portion.

19. The orthodontic archwire of claim 18, wherein the archwire has an overall, generally U-shaped configuration with a pair of distal end sections and an anterior section interconnecting the distal end sections, and wherein the anterior section has a stiffness that is less than the stiffness of either of the distal end sections.

20. The orthodontic archwire of claim 18, wherein the intermediate portion comprises a metal braze.

21. The orthodontic archwire of claim 18, wherein the labial portion includes a recess.

22. The orthodontic archwire of claim 21, and including a coating received in the recess.

23. The orthodontic archwire of claim 22 wherein the coating and the intermediate portion are made of the same material.

* * * * *

UNITED STATES PATENT AND TRADEMARK OFFICE
CERTIFICATE OF CORRECTION

PATENT NO.    : 6,095,809
DATED         : August 1, 2000
INVENTOR(S)   : John S. Kelly et al.

It is certified that error appears in the above-identified patent and that said Letters Patent is hereby corrected as shown below:

Column 4,
Line 20, please delete "10" before "each of the…..".

Signed and Sealed this

Thirtieth Day of December, 2003

JAMES E. ROGAN
*Director of the United States Patent and Trademark Office*